(12) United States Patent
Chi et al.

(10) Patent No.: US 9,381,369 B2
(45) Date of Patent: Jul. 5, 2016

(54) BATTERY FOR USE WITH MEDICAL DEVICES

(71) Applicant: Cardiac Pacemakers, Inc., St. Paul, MN (US)

(72) Inventors: Ignacio Chi, Mahtomedi, MN (US); Joseph C. Delmedico, Lino Lakes, MN (US); Brian L. Schmidt, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/616,141

(22) Filed: Feb. 6, 2015

(65) Prior Publication Data
US 2015/0221898 A1    Aug. 6, 2015

Related U.S. Application Data

(60) Provisional application No. 61/936,409, filed on Feb. 6, 2014.

(51) Int. Cl.
*A61N 1/00* (2006.01)
*A61N 1/378* (2006.01)
*H01M 2/16* (2006.01)
(Continued)

(52) U.S. Cl.
CPC ............ *A61N 1/3787* (2013.01); *H01M 2/026* (2013.01); *H01M 2/0232* (2013.01); *H01M 2/0272* (2013.01); *H01M 2/1686* (2013.01); *H01M 2/26* (2013.01); *H01M 4/043* (2013.01); *H01M 4/048* (2013.01); *H01M 4/10* (2013.01); *H01M 4/405* (2013.01); *H01M 4/48* (2013.01); *H01M 4/502* (2013.01); *H01M 4/54* (2013.01); *H01M 4/58* (2013.01); *H01M 4/5835* (2013.01); *H01M 4/75* (2013.01); *H01M 2/065* (2013.01); *H01M 2/1653* (2013.01); *H01M 2/361* (2013.01); *H01M 2/365* (2013.01); *H01M 4/661* (2013.01);
(Continued)

(58) Field of Classification Search
CPC ............... A61M 25/00; A61N 1/3787; H01M 2220/30; H01M 2/0232; H01M 2/026; H01M 2/0272; H01M 2/065; H01M 2/1653; H01M 2/1686; H01M 2/26; H01M 2/361; H01M 2/365; H01M 4/043; H01M 4/048; H01M 4/10; H01M 4/405; H01M 4/48; H01M 4/502; H01M 4/54; H01M 4/58; H01M 4/5835; H01M 4/661; H01M 4/75; Y10T 29/4911
See application file for complete search history.

(56) References Cited

U.S. PATENT DOCUMENTS

| | | |
|---|---|---|
| 6,235,422 B1 | 5/2001 | Kaplan et al. |
| 2004/0258982 A1 | 12/2004 | Coffey et al. |
| 2014/0329126 A1* | 11/2014 | Ho et al. .............. 429/128 |

FOREIGN PATENT DOCUMENTS

JP    2009212051 A    9/2009

OTHER PUBLICATIONS

International Search Report for International application No. PCT/US2015/014864 dated Apr. 28, 2015, 2 pages.

*Primary Examiner* — George Manuel
(74) *Attorney, Agent, or Firm* — Seager, Tufte & Wickhem LLP.

(57) ABSTRACT

Medical devices and batteries for use with medical devices are disclosed. An example battery may include a housing. A plurality of cathode pellets may be disposed within the housing. An anode may extend through at least some of the plurality of cathode pellets. A lid may be attached to the housing.

19 Claims, 7 Drawing Sheets

(51) Int. Cl.
  *H01M 2/02* (2006.01)
  *H01M 2/26* (2006.01)
  *H01M 4/04* (2006.01)
  *H01M 4/10* (2006.01)
  *H01M 4/40* (2006.01)
  *H01M 4/48* (2010.01)
  *H01M 4/50* (2010.01)
  *H01M 4/54* (2006.01)
  *H01M 4/58* (2010.01)
  *H01M 4/583* (2010.01)
  *H01M 4/75* (2006.01)
  *H01M 2/06* (2006.01)
  *H01M 2/36* (2006.01)
  *H01M 4/66* (2006.01)
  *H01M 4/02* (2006.01)

(52) U.S. Cl.
  CPC ..... *H01M2004/021* (2013.01); *H01M 2220/30* (2013.01); *Y10T 29/4911* (2015.01)

BATTERY FOR USE WITH MEDICAL DEVICES

CROSS-REFERENCE TO RELATED APPLICATIONS

This application claims priority under 35 U.S.C. §119 to U.S. Provisional Application Ser. No. 61/936,409, filed Feb. 6, 2014, the entirety of which is incorporated herein by reference.

TECHNICAL FIELD

The present disclosure pertains to batteries. More particularly, the present disclosure pertains to batteries for use with medical devices.

BACKGROUND

A wide variety of medical devices have been developed for medical use. Some of these devices include implantable medical devices. Such devices may include a power source or battery. These devices are manufactured by any one of a variety of different manufacturing methods and may be used according to any one of a variety of methods. Of the known medical devices, batteries, and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices and/or batteries for use with medical devices. A battery for use with a medical device is disclosed. The battery comprises:
 a housing;
 a plurality of cathode pellets disposed within the housing;
 an anode extending through at least some of the plurality of cathode pellets; and
 a lid attached to the housing.

Alternatively or additionally to any of the embodiments above, the housing includes titanium, a titanium alloy, aluminum, or an aluminum alloy.

Alternatively or additionally to any of the embodiments above, the cathode pellets include carbon monofluoride, manganese dioxide, silver vanadium oxide, copper fluoride, or combinations thereof.

Alternatively or additionally to any of the embodiments above, the cathode pellets includes one or more additives.

Alternatively or additionally to any of the embodiments above, the plurality of cathode pellets includes three or more cathode pellets.

Alternatively or additionally to any of the embodiments above, the plurality of cathode pellets includes four or more cathode pellets.

Alternatively or additionally to any of the embodiments above, the anode includes lithium and/or a lithium alloy.

Alternatively or additionally to any of the embodiments above, the anode includes a first half cylinder and a second half cylinder coupled to the first half cylinder.

Alternatively or additionally to any of the embodiments above, the anode includes a porous polymeric separator.

Alternatively or additionally to any of the embodiments above, the porous polymeric separator includes a plurality of layers.

Alternatively or additionally to any of the embodiments above, the anode includes a first pin comprising nickel, stainless steel, or molybdenum.

Alternatively or additionally to any of the embodiments above, further comprising a feed-through member having a second pin, wherein the second pin is coupled to the first pin.

Alternatively or additionally to any of the embodiments above, a connecting sleeve is coupled to the first pin.

Alternatively or additionally to any of the embodiments above, further comprising a feed-through member having a second pin, wherein the second pin is coupled to the connecting sleeve.

Alternatively or additionally to any of the embodiments above, an electrolyte is disposed within the housing and positioned adjacent to the cathode pellets, the anode, or both.

Alternatively or additionally to any of the embodiments above, the housing includes an interior conductive carbon coating.

Alternatively or additionally to any of the embodiments above, the plurality of cathode pellets having a pore structure with substantially uniform pore sizes.

An implantable medical device is disclosed. The implantable medical device comprises:
 a device body; and
 a battery disposed within the device body, wherein the battery comprises:
 a housing,
 a plurality of cathode pellets disposed within the housing,
 an anode extending through at least some of the plurality of cathode pellets, and
 a lid attached to the housing.

A battery for use with an implantable medical device is disclosed. The battery comprises:
 a housing;
 a plurality of cylindrical cathode pellets disposed within the housing, the cylindrical cathode pellets each defining a lumen;
 wherein the cylindrical cathode pellets have a pore structure with substantially uniform pore sizes;
 an anode extending through the lumen of each of the cylindrical cathode pellets; and
 a lid attached to the housing.

Alternatively or additionally to any of the embodiments above, the housing includes titanium, a titanium alloy, aluminum, or an aluminum alloy.

Alternatively or additionally to any of the embodiments above, the cylindrical cathode pellets include carbon monofluoride.

Alternatively or additionally to any of the embodiments above, the anode includes lithium and/or a lithium alloy.

Alternatively or additionally to any of the embodiments above, the anode includes a porous polymeric separator.

Alternatively or additionally to any of the embodiments above, the anode includes a first pin comprising nickel, stainless steel, or molybdenum;
 wherein a connecting sleeve is coupled to the first pin; and
 further comprising a feed-through member having a second pin, wherein the second pin is coupled to the connecting sleeve.

Alternatively or additionally to any of the embodiments above, an electrolyte is disposed within the housing and positioned adjacent to the cylindrical cathode pellets, the anode, or both.

Alternatively or additionally to any of the embodiments above, the housing includes an interior conductive carbon coating.

An implantable medical device is disclosed. The implantable medical device comprises:
a device body; and
a battery disposed within the device body, wherein the battery comprises:
a housing,
a plurality of cylindrical cathode pellets disposed within the housing, the cylindrical cathode pellets each defining a lumen,
wherein the cylindrical cathode pellets have a pore structure with substantially uniform pore sizes,
an anode extending through the lumen of each of the cylindrical cathode pellets, and
a lid attached to the housing.

Alternatively or additionally to any of the embodiments above, the device body includes a cardiac pacemaker, a leadless cardiac pacemaker, or an implantable cardioverter defibrillator.

A method for manufacturing a battery is disclosed. The method comprises:
press forming a powder into a cylindrical cathode pellet;
transferring the cylindrical cathode pellet into a housing;
press forming one or more additional cylindrical cathode pellets and transferring the one or more additional cylindrical cathode pellets into the housing; and
extending an anode through the cylindrical cathode pellets.

A battery for use with a medical device is disclosed. The battery comprises:
a housing;
a plurality of cathode pellets disposed within the housing;
an anode extending through at least some of the plurality of cathode pellets;
a feed-through member having a pin member, the pin member extending into the anode; and
a lid attached to the housing.

Alternatively or additionally to any of the embodiments above, the pin member comprises nickel, stainless steel, or molybdenum.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
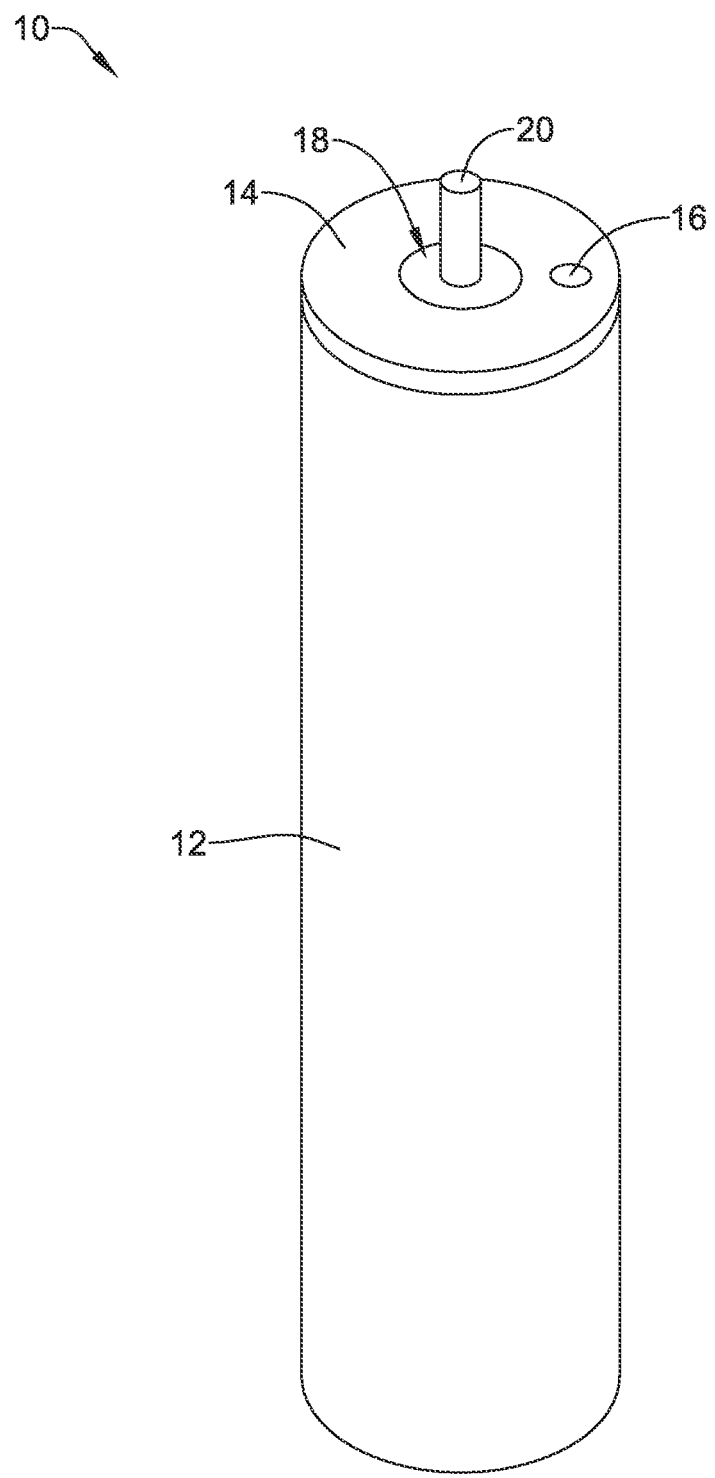
FIG. 1 is a side view of an example battery.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cardiac pacemakers and/or other implantable medical devices provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition.

The power source (e.g., that may take the form of a battery) for cardiac pacemakers, leadless cardiac pacemakers, and/or other implantable medical devices is generally disposed within the housing of the implantable medical device. For a number of reasons, it may be desirable for the battery to be designed to delivery suitable power, have a relatively compact shape and/or configuration, and otherwise provide consistent, reliable power. The batteries disclosed herein (and/or medical devices utilizing such batteries) are designed with at least some of these and other goals in mind.

FIG. 1 is a side view of an example battery 10. Battery 10 may include a "can" or housing 12. A lid or cap 14 may be coupled to housing 12. Cap 14 may include an opening 16 that may be used, for example, for disposing a material such as an electrolyte within housing 12. A feed-through or transition member 18 may be coupled to cap 14. Feed-through 18 may include a pin member 20. In use, battery 10 may be disposed within the housing of a medical device in order to provide power to the medical device. For example, battery 10 may be utilized with a cardiac pacemaker, a leadless cardiac pacemaker, an implantable cardioverter defibrillator (ICD), and the like, or other types of medical devices and/or implantable medical devices. This may include disposing battery 10 with a housing or portion of the device, attaching battery 10 to the device, or otherwise electrically coupling battery 10 to the device.

Housing 12 may take the form of a cylinder with a closed end or "bottom". Housing 12 may be formed from a suitable material such as titanium, a titanium alloy, aluminum, an aluminum alloy, combinations thereof, or the like. These are just examples. Other materials are contemplated. Housing 12 may serve as the cathode current collector. As described herein, housing 12 may include a conductive coating that electrically couples housing 12 with the cathode (e.g., the cathode pellets 22, which can be seen in FIG. 2).

Figure 2:
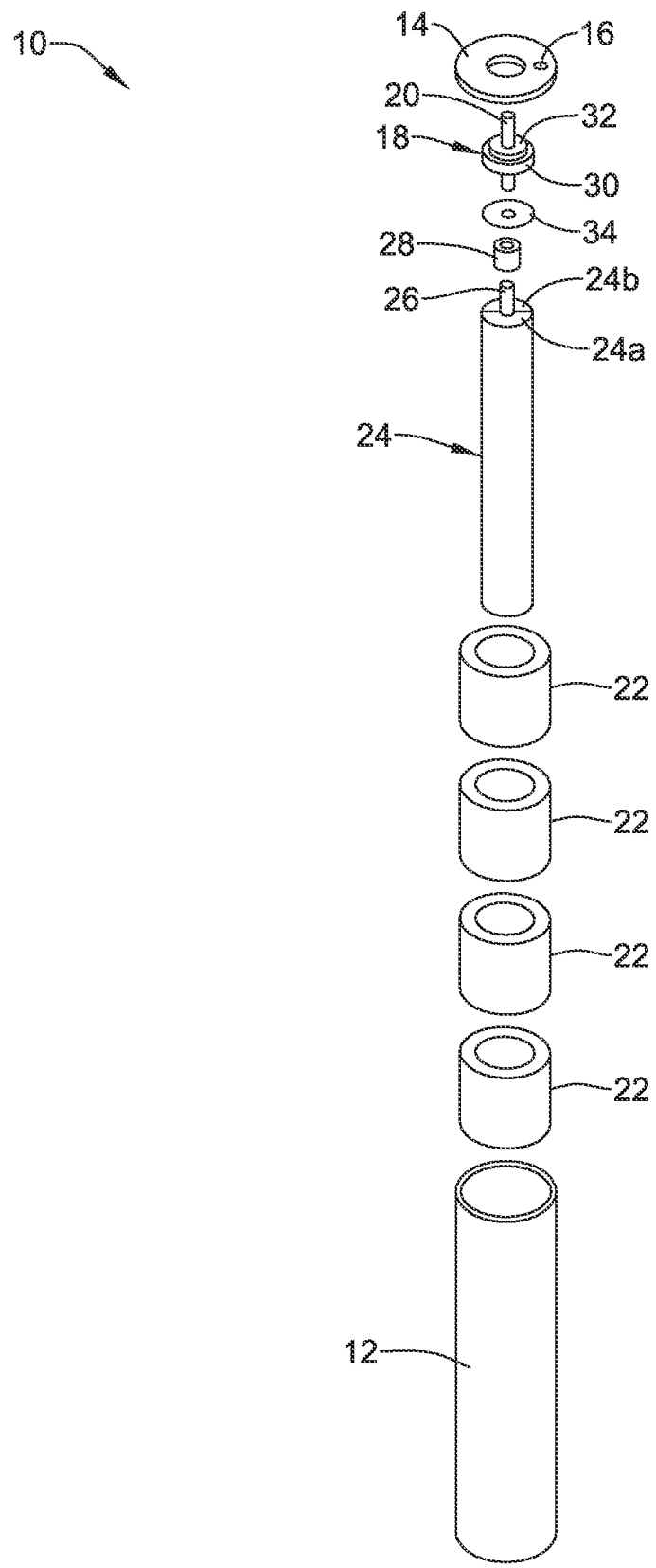
FIG. 2 is an exploded view of an example battery.

Some of the other structural features of battery 10 can be seen in FIG. 2. For example, battery 10 may include a plurality of cathode pellets 22. The number of pellets 22 utilized can vary. For example, one, two, three, four, five, six, seven, eight, or more cathode pellets 22 can be used. In at least some embodiments, pellets 22 may include a suitable material such as carbon monofluoride powder, manganese dioxide ($MnO_2$, for example, which can be used in applications where higher discharge rates are desired), silver vanadium oxide, copper fluoride, combinations thereof, or the like. The material may be pressed or otherwise formed into a desired shape. This may include press forming, molding, mechanically forming the material in a desired shape (e.g., drilling a cylindrical rod so as to form a "hollow" cylinder), or the like. The desired shape may vary. For example, pellets 22 may be formed to have a generally hollow cylindrical shape (e.g., a cylinder with an opening through the middle). Other shapes are contemplated including regular shapes, geometric shapes, irregular shapes, etc.

The use of pellets 22 may be desirable for a number of reasons. For example, pellets 22 may have a pore structure with a number of pores. By using a plurality of discrete pellets 22 rather than a singular (e.g., and larger) cathode, pellets 22 may be less likely to be deformed or otherwise may be capable of more efficiently distributing compressive forces when pellets 22 are disposed within housing 12. Because of this, the pores may be able to have and maintain a pore distribution where the pores have substantially uniform pore sizes. Accordingly, pellets 22 may be able to more efficiently be used to generate a current for battery 10.

An anode 24 may be disposed within housing 12. In at least some embodiments, anode 24 may include lithium and/or a lithium alloy. Other materials may also be used. Anode 24 may include one or more sections such as sections 24a/24b that formed from lithium foils using a die. For example, two 0.020 inch thick lithium foils may be formed into two half cylinder sections 24a/24b that are coupled to one another. Sections 24a/24b may be pressed onto a pin 26. Pin 26 may take the form of a wire formed from nickel, stainless steel (e.g., 316L stainless steel), molybdenum, or the like. Pin 26 may be a relatively thin wire. For example, pin 26 may be about 0.01-0.02 inches in diameter, or about 0.015 inches in diameter. These are just examples.

Feed-through 18 may include a first portion 30 and a second portion 32. In at least some embodiments, first portion 30 may include a metal. For example, first portion 30 may include titanium. Second portion 32 may include a non-conductive material such as glass. Feed-through 18 may connect with anode 24 through a connecting sleeve 28. For example, connecting sleeve 28 may be coupled to pin 26 (of anode 24) and to pin member 20 (of feed-through 18). Cap 14 may fit over feed-through 18 and close off or seal housing 12. In at least some embodiments, a gasket 34 may be disposed between connecting sleeve 28 and feed-through 18. Pin 20 may be formed from the same or similar materials as pin 26. For example, pin 20 may be formed from nickel, stainless steel (e.g., 316L stainless steel), molybdenum, or the like.

Figure 3:
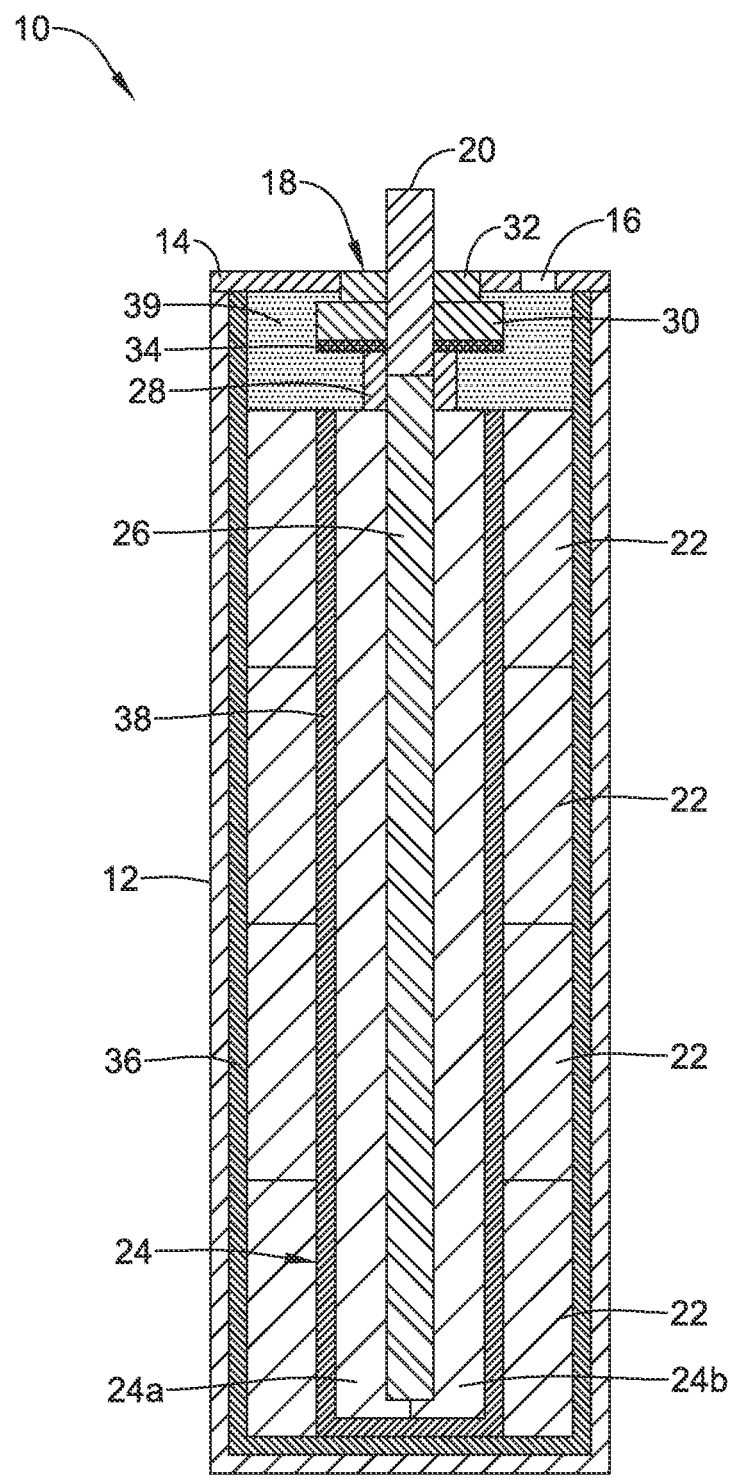
FIG. 3 is a cross-sectional view of an example battery.
Figure 3A:
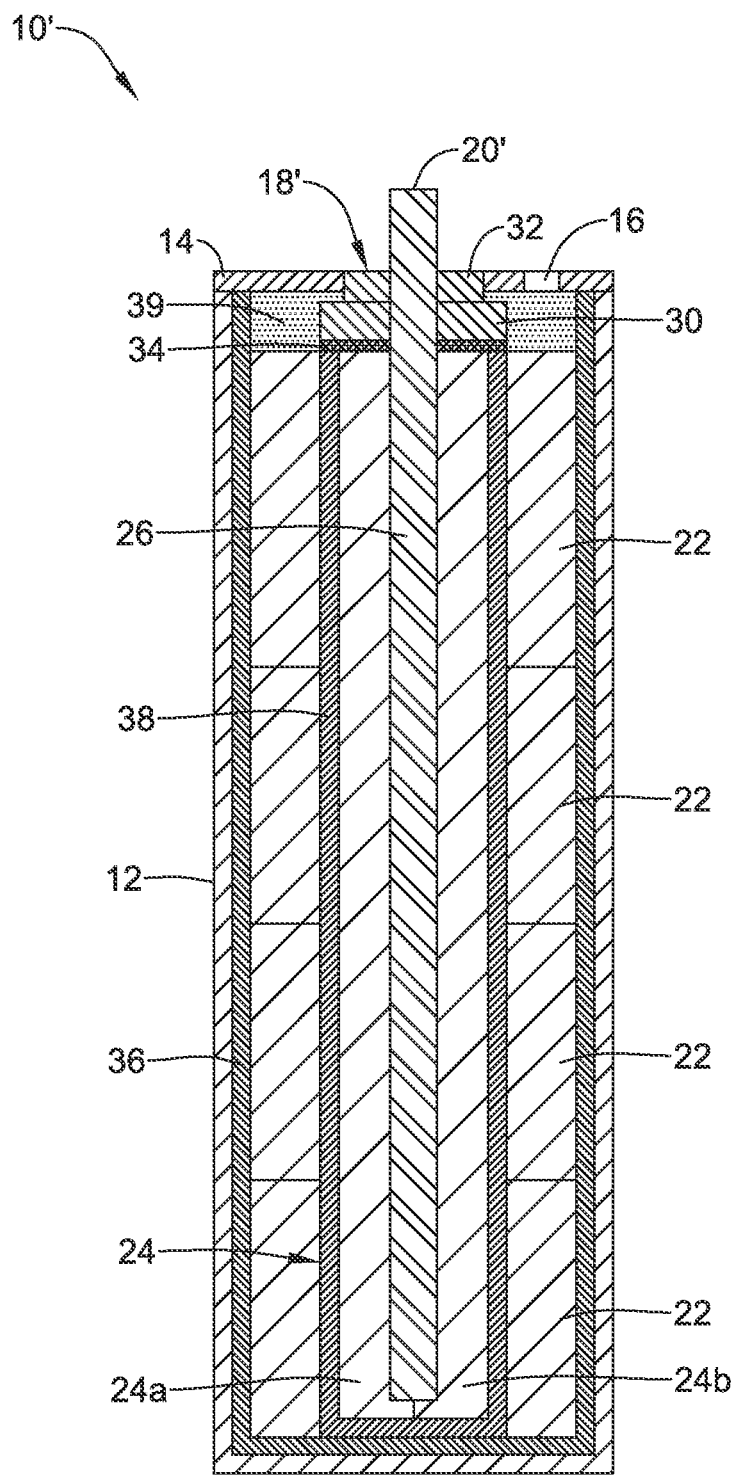
FIG. 3A is a cross-sectional view of an example battery.

FIG. 3A illustrates an example battery 10' that may be similar to other batteries disclosed herein. Battery 10' may include feed-through 18' with pin 20'. Pin 20' (which may include molybdenum or other materials such as those disclosed herein) may extend into and electrically couple with anode 24. In other words, pin 20' may be longer than pin 20 so that pin 20' extends into anode 24. Accordingly, pin 20' may serve as the anode current collector and pin 26 (as well as connecting sleeve 28) may be omitted from battery 10'.

As seen in FIG. 3, housing 12 may include an inner coating 36. Coating 36 may take the form of a conductive material such as a conductive carbon ink. Other materials are contemplated. Anode 24 may include a wrap or separator 38. Generally, separator 38 may take the form of an insulating material that may insulate anode 24 from portions of housing 12. In at least some embodiments, separator 38 include a porous polymeric material including one or more layers. For example, separator 38 may include a polyethylene material sandwiched between two layers of polypropylene. Other materials are contemplated.

An electrolyte 39 may be disposed within housing 12 via opening 16. Electrolyte 39 may include a suitable material such as 1M $LiBF_4$ in gamma butyrolactone and dimethoxyethane (50/50 by volume). Opening 16 may be welded (e.g., spot welded then laser welded) to seal opening 16 after disposing electrolyte 39 through opening 16.

As indicated herein, battery 10 may have a suitable size and shape for use with a medical device. For example, battery 10 may have a diameter in the range of about 0.15 to 0.35 inches, or about 0.20 to 0.25 inches. Battery 10 may have a height of about 0.35 to 1.15 inches, or about 0.5 to 1 inches. One example battery 10 may have a diameter of 0.213 inches and a height of 0.962 inches. This example battery 10 may utilize 4 cathode pellets 22 and may have a capacity of about 175 mAh (e.g., about 312 mAh/cc). Another example battery 10 may have a diameter of 0.226 inches and a height of 0.557 inches. This example battery may have a capacity of about 88 mAh. These are just examples. Other dimensions are contemplated.

Figure 4:
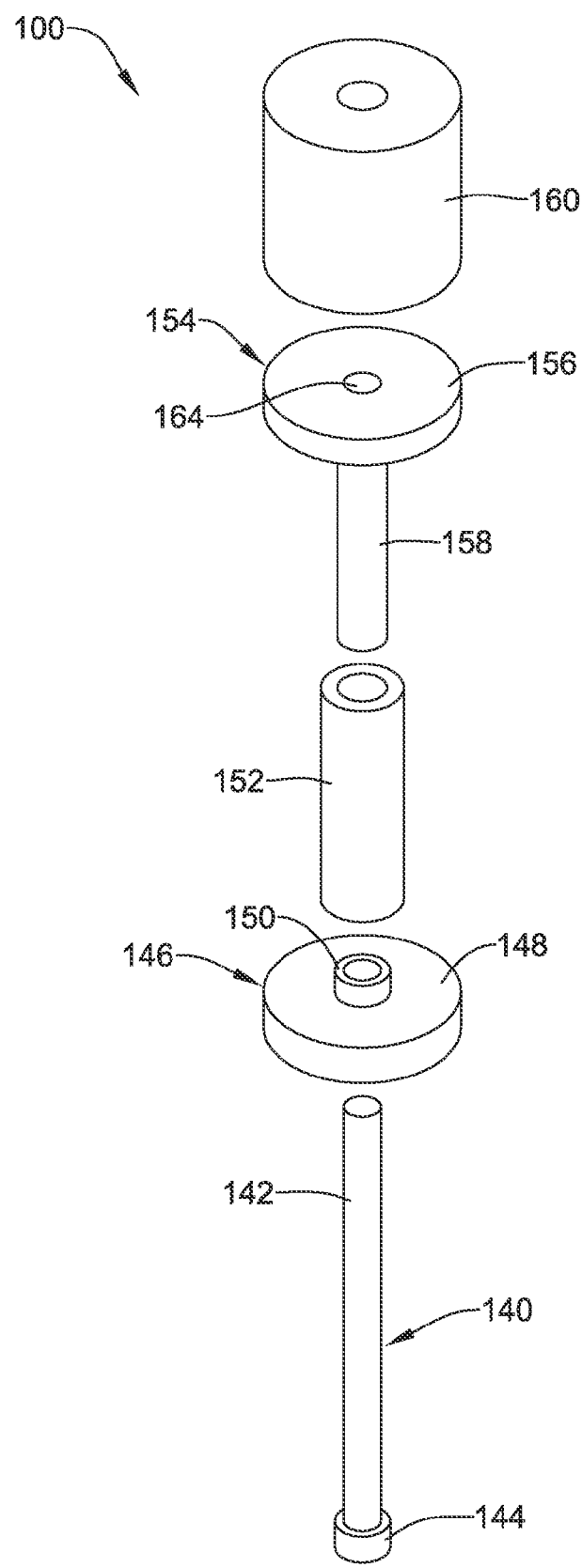
FIGS. 4-6 illustrate an example assembly for manufacturing at least a portion of a battery.
Figure 5:
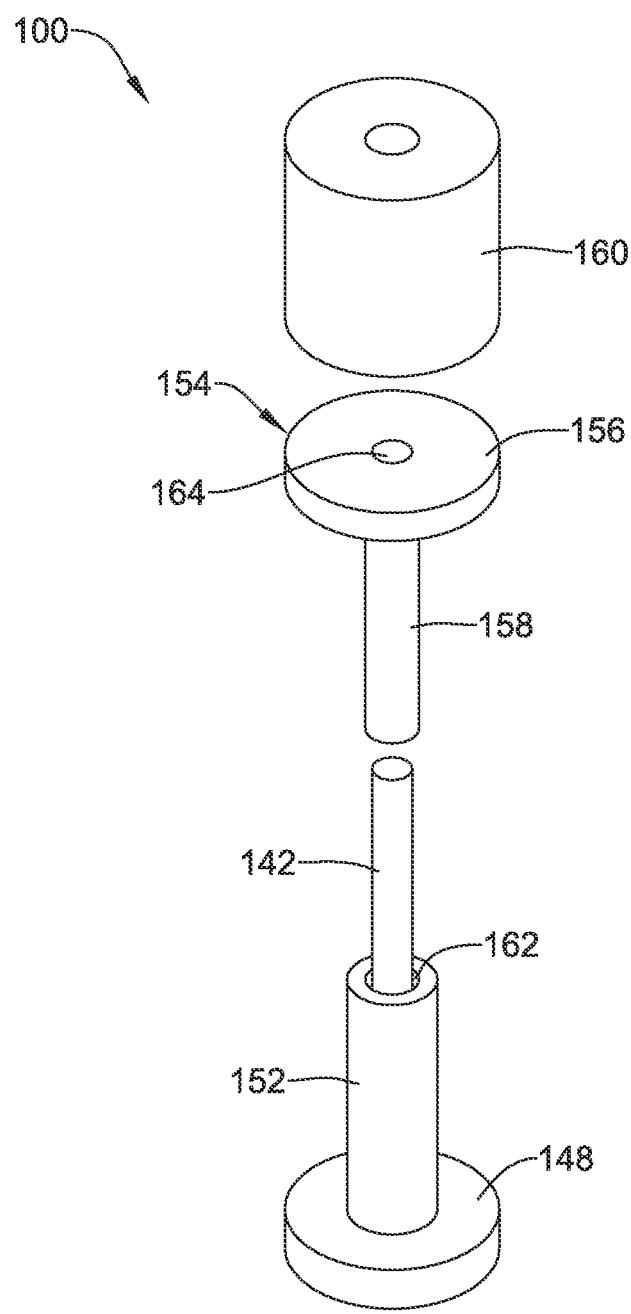
Figure 6:
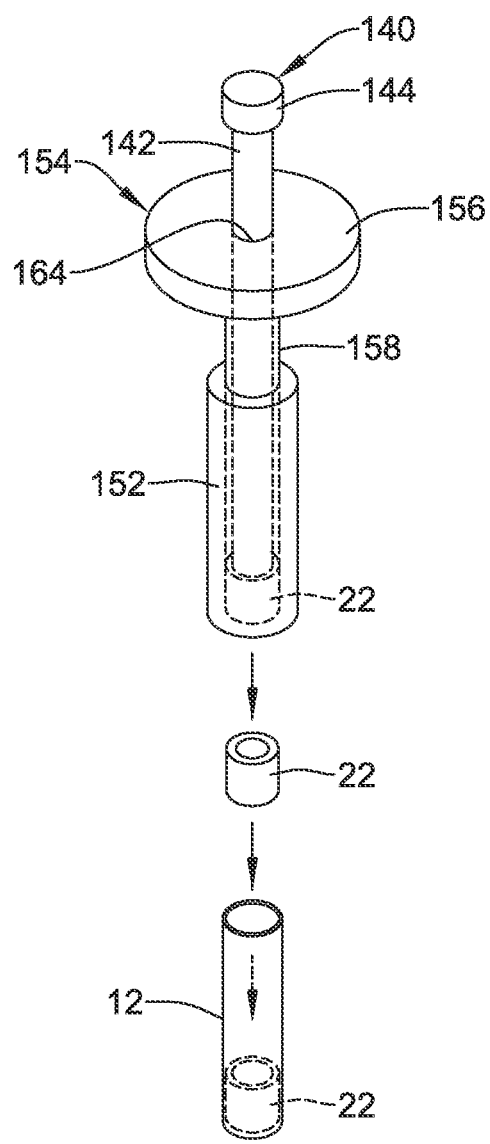

FIGS. 4-6 illustrate an example assembly 100 for manufacturing at least a portion of battery 10 and/or other batteries. Assembly 100 may include base assembly 146 having a base portion 148 a support portion 150. A cylindrical member 152 may be coupled to base assembly 146, for example along support portion 150. A pin assembly 140 may extend through base assembly 146. Pin assembly 140 may include a pin member 142 and a base 144.

A compacting member or stamping member 154 having a top portion 156 and a compacting portion 158 may be used to compact material within cylindrical member 152. An opening 164 may be formed in stamping member 154. In some instances, a weight 160 may be used to apply addition force onto stamping member 154.

When assembled, pin member 142 may be coupled to base portion 148 and extend through cylindrical member 152 as shown in FIG. 5. Cylindrical member 152 may have an opening or chamber 162 defined therein. The material used to form cathode pellets 22 may be fed into chamber 162 (e.g., using a funnel or other suitable mechanism). After the material is loaded, stamping member 154 may be used to form the material into a suitable cathode pellet (e.g., pellet 22). After compacting material within chamber 162, pin assembly 140 may be pulled from base assembly 146 and then inserted into opening 164 and through pellet 22 (e.g., to help maintain the shape of pellet 22 during the transfer). Stamping member 154 may be then utilized to transfer or "push" cathode pellet 22 into housing 12. Depending on the number of pellets 22 utilized, the process may be repeated one or more times in order to load the desired number of pellets 22 into housing 12.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A battery for use with a medical device, the battery comprising:
    a housing comprising an interior conductive carbon coating;
    a plurality of cathode pellets disposed within the housing;
    an anode extending through at least some of the plurality of cathode pellets; and
    a lid attached to the housing.

2. The battery of claim 1, wherein the housing includes titanium, a titanium alloy, aluminum, or an aluminum alloy.

3. The battery of claim 1, wherein the cathode pellets include carbon monofluoride, manganese dioxide, silver vanadium oxide, copper fluoride, or combinations thereof.

4. The battery of claim 3, wherein the cathode pellets includes one or more additives.

5. The battery of claim 1, wherein the plurality of cathode pellets includes three or more cathode pellets.

6. The battery of claim 1, wherein the plurality of cathode pellets includes four or more cathode pellets.

7. The battery of claim 1, wherein the anode includes lithium and/or a lithium alloy.

8. The battery of claim 1, wherein the anode includes a porous polymeric separator.

9. The battery of claim 8, wherein the porous polymeric separator includes a plurality of layers.

10. The battery of claim 1, wherein the anode includes a first pin comprising nickel, stainless steel, or molybdenum.

11. The battery of claim 10, further comprising a feedthrough member having a second pin, wherein the second pin is coupled to the first pin.

12. The battery of claim 10, wherein a connecting sleeve is coupled to the first pin.

13. The battery of claim 12, further comprising a feedthrough member having a second pin, wherein the second pin is coupled to the connecting sleeve.

14. The battery of claim 1, wherein an electrolyte is disposed within the housing and positioned adjacent to the cathode pellets, the anode, or both.

15. The battery of claim 1, wherein the plurality of cathode pellets having a pore structure with substantially uniform pore sizes.

16. A battery for use with a medical device, the battery comprising:
    a housing;
    a plurality of cathode pellets disposed within the housing;
    an anode extending through at least some of the plurality of cathode pellets, wherein each anode includes a first half cylinder and a second half cylinder coupled to the first half cylinder; and
    a lid attached to the housing.

17. An implantable medical device, comprising:
    a device body; and
    a battery disposed within the device body, wherein the battery comprises:
        a housing,
        a plurality of cylindrical cathode pellets disposed within the housing, the cylindrical cathode pellets each defining a lumen,
        wherein the cylindrical cathode pellets have a pore structure with substantially uniform pore sizes,
        an anode extending through the lumen of each of the cylindrical cathode pellets, and
        a lid attached to the housing.

18. The implantable medical device of claim 17, wherein the device body includes a cardiac pacemaker, a leadless cardiac pacemaker, or an implantable cardioverter defibrillator.

19. A method for manufacturing a battery, the method comprising:
    press forming a powder into a cylindrical cathode pellet;
    transferring the cylindrical cathode pellet into a housing;
    press forming one or more additional cylindrical cathode pellets and transferring the one or more additional cylindrical cathode pellets into the housing; and
    extending an anode through the cylindrical cathode pellets;
    attaching a lid to the housing.

* * * * *